United States Patent
Hershgordon

[11] Patent Number: 5,920,932
[45] Date of Patent: Jul. 13, 1999

[54] SLEEPING PILLOW INSERT AND AN ENLARGED PILLOW CASE, FOR REDUCING SNORING

[76] Inventor: Robert Hershgordon, 2277 Maltese Ct., Bensalem, Pa. 19020

[21] Appl. No.: 08/782,802

[22] Filed: Jan. 13, 1997

[51] Int. Cl.[6] .................................................. A47G 9/00
[52] U.S. Cl. .................................... 5/636; 5/640; 5/490
[58] Field of Search ........................ 5/636, 640, 643, 5/645, 637, 639, 490; D6/601

[56] References Cited

U.S. PATENT DOCUMENTS

| | | | |
|---|---|---|---|
| D. 47,140 | 3/1915 | Newkirk | D6/601 |
| D. 118,319 | 12/1939 | Kandell | D6/601 |
| D. 272,187 | 1/1984 | Broomes | D24/191 |
| D. 330,989 | 11/1992 | Evans | D6/601 |
| 599,850 | 3/1898 | Larrabee et al. | 5/643 |
| 2,880,428 | 4/1959 | Forsland | 5/636 |
| 3,829,917 | 8/1974 | De Laittre et al. | |
| 4,118,813 | 10/1978 | Armstrong | |
| 4,227,270 | 10/1980 | Rivera | 5/636 |
| 4,536,905 | 8/1985 | De Santis | |
| 4,550,459 | 11/1985 | Endel et al. | |
| 4,748,702 | 6/1988 | Sandler | |
| 4,754,513 | 7/1988 | Rinz | 5/490 |
| 4,832,007 | 5/1989 | Davis, Jr. et al. | |
| 4,850,067 | 7/1989 | Lattore | |
| 4,908,894 | 3/1990 | Sanders | 5/640 |
| 5,020,174 | 6/1991 | Sarkozi | |
| 5,535,467 | 7/1996 | Ciske | 5/643 |

*Primary Examiner*—Alexander Grosz

[57] ABSTRACT

A pillowcase insert, comprised of a wedge member resting on a sheet member, and an enlarged horizontally opening pillowcase, which when assembled with an ordinary sleeping pillow, will reduce the incidence of snoring and improve the sleep of the user.

11 Claims, 4 Drawing Sheets

SLEEPING PILLOW INSERT AND AN ENLARGED PILLOW CASE, FOR REDUCING SNORING

BACKGROUND OF THE INVENTION

FIELD OF THE INVENTION

This invention relates to the art of sleeping pillows, and more particularly, to the art of cervical pillows providing corrective support with the additional benefit of reducing the incidence of snoring because it will reduce the likelihood of the airways being constricted and by improving the sleeping position of a supine sleeper.

People generally become very attached to their own sleeping pillow because getting a good night sleep generally is related to the regimen that has been established over the years. Most people would not give up the most important part of their sleep regimen if there was another way. An enlarged pillow case is necessary because by adding the wedge member assembly to the ordinary sleeping pillow a conventional pillow case would not be able to accommodate the increased size of the device. By using a device that can be inserted into an enlarged pillowcase with their own pillow the user's sleep regimen receives the least disturbance than with changing their pillow entirely.

DESCRIPTION OF THE PRIOR ART

Rinz, U.S. Pat. No. 4,754,513 discloses a pillow insert that has a half round shape that rests upon an ordinary pillow to convert it into an orthopedic pillow. This does not take into account the thickness of the ordinary pillow and cannot provide a consistency of the height of the final device.

Other similar devices such as Sandler, U.S. Pat. No. 4,748,702 requires the snorer to give up their personal pillow and to suffer discomfort if they reposition themselves while asleep thus disturbing their sleep. DeSantis U.S. Pat. No. 4,536,905 uses not only a new pillow but the addition of a semi-soft brace placed above a shoulder slot which caused discomfort to the subject's head in a dorsal position. Latorre U.S. Pat. No. 4,850,067, Armstrong U.S. Pat. No. 4,118,813 again requires the snorer to give up their personal pillow to use their devise. Rivera U.S. Pat. No. 4,227,270, teaching the use of a pillow with the case having a sheet extending beyond the pillow's edge, is cited as relevant art.

SUMMARY OF THE INVENTION

Among the objectives of the present invention are to provide a conventional and inexpensive, removable pillow insert for converting an ordinary sleeping pillow and an enlarged pillow case into an anti snoring device.

By combining a ¼ cylindrical 4 inch high piece of foam material that is 12 to 20 inches long, a 12 to 20×24 inch piece of quarter inch high foam, an enlarged pillow case with a finished size of 22 inches in length and 26 to 36 inches in width, and an ordinary sleeping pillow, this invention will provide a unique and inexpensive orthopedic device that will reduce the incidence of snoring.

DESCRIPTION OF THE PREFERRED EMBODIMENTS

This is a device that is inserted into an enlarged pillowcase that can convert a normal pillow into a cervical pillow with the ability to reduce the incidence of snoring of the user. This is accomplished by improving the angle of the head and neck thus reducing the chance of constriction of the aired flow to the lungs. It then allows the individual to breathe through their nose and reduce the incidence of snoring.

Figure 1:
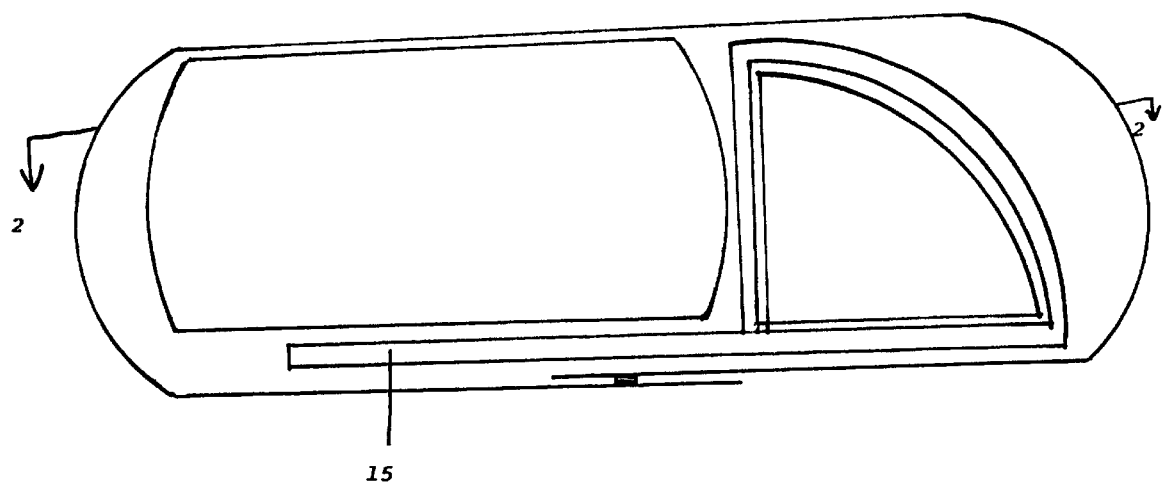
FIG. 1 is a side view of the invention.
Figure 3:
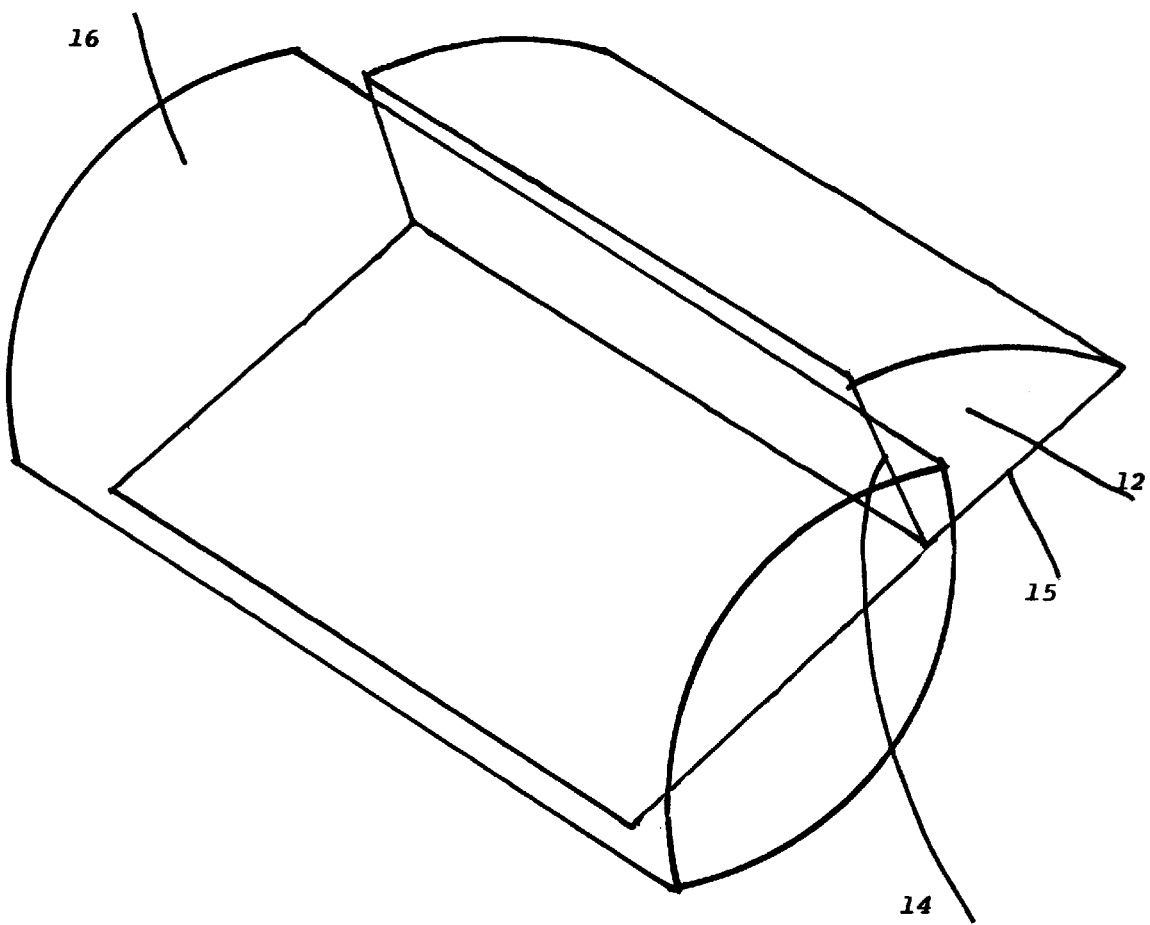
FIG. 3 is a perspective view of the invention.

As shown in FIG. 1, which is an end view of the assembly made according to the present invention, and in FIG. 3, which is a perspective view, the invention includes a wedge member 12 which is constructed of resilient foam rubber. In particular, wedge member 12 has a quarter-cylindrical shape in which the radius of cylinder is preferably approximately four inches. The width of the wedge member 12 is preferably 12 to 20 inches. The wedge member 12 includes a first flat surface 21, a second flat surface 22 and a curved surface 23.

Figure 2:
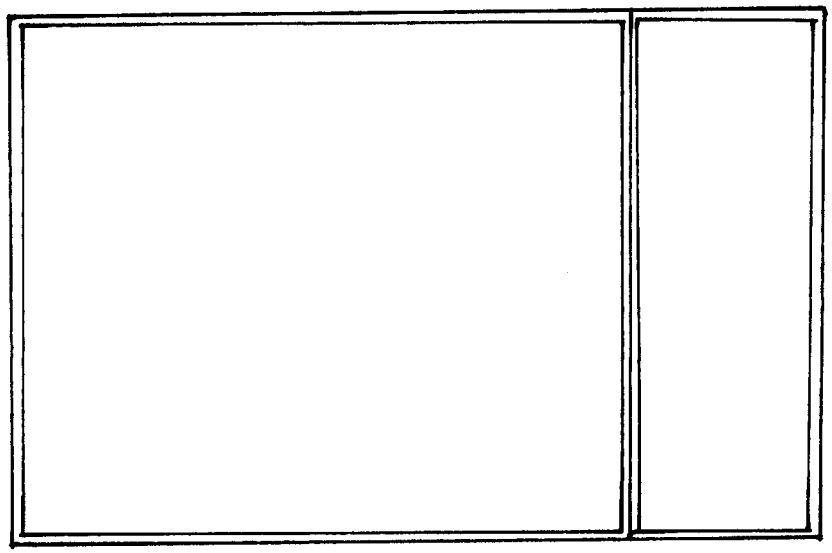
FIG. 2 is a view of the invention taken along lines "2—2" of FIG. 1.

The present invention also includes a sheet member 14, which is also preferably constructed of resilient foam rubber. Sheet member 14, is preferably one quarter-inch thick and has initial dimensions which are selected to correspond to the dimensions chosen from the wedge member 12. In particular, the overall length of the sheet member 14 will preferably be approximately 24 inches. The width of the sheet member 14 will preferably correspond to the with of the wedge member 12, as best seen in FIG. 2, which is a cross-sectional view taken along arrows 2—2 in FIG. 1. Thus, if the wedge member 12 is chosen to have a width of 12 inches, the sheet member 14 will likewise have a width of 12 inches.

Wedge member 12 and sheet member 14 are assembled together by wrapping the sheet member around the outer surfaces of the wedge member 12 as best shown in FIGS. 1 and 3. The sheet member is fixedly attached to the wedge member 12 through any conventional means, such as adhesive material. As shown in FIG. 1, the sheet member 14 is placed against the flat surface 21 so that the leading edge of sheet member 14 is proximate the corner at which the first and second flat surfaces 21, 22 meet. The sheet member 14 is then wrapped around the curved surface 23 and then the second flat surface 22.

The resultant assembly will thus leave the sheet member 14 fully wrapped around the wedge member 12, with the sheet member 14 extending substantially beyond the perimeter of the wedge member 12 to form extended portion 15. As will be appreciated by one skilled in the art, if the sheet member 14 has an initial length of 24 inches, and one end is wrapped around the wedge member 12 which has a radius of approximately four inches, extended portion 15 will extend approximately ten inches away from the wedge member 12.

As further shown in FIGS. 1 and 2, a conventional pillow 16 may then be rested on the upper surface of the extended portion 15 of the sheet member 14, and abutting the wrapped first flat surface 21 of the wedge member 12. As shown in FIGS. 1 and 2, the pillow 16 may protrude over and extend from the outer limits of the sheet member 14. What is essential, however, is that there be a substantial area in which the lower surface of the pillow 16 abuts against the upper surface of the extended portion 15 of the sheet member 14. The natural friction that results from the fabric covering of pillow 16 and the foam rubber from which the sheet member 14 is made will substantially prevent relative movement between the pillow 16 and the extended portion of the sheet member 14.

Figure 4:
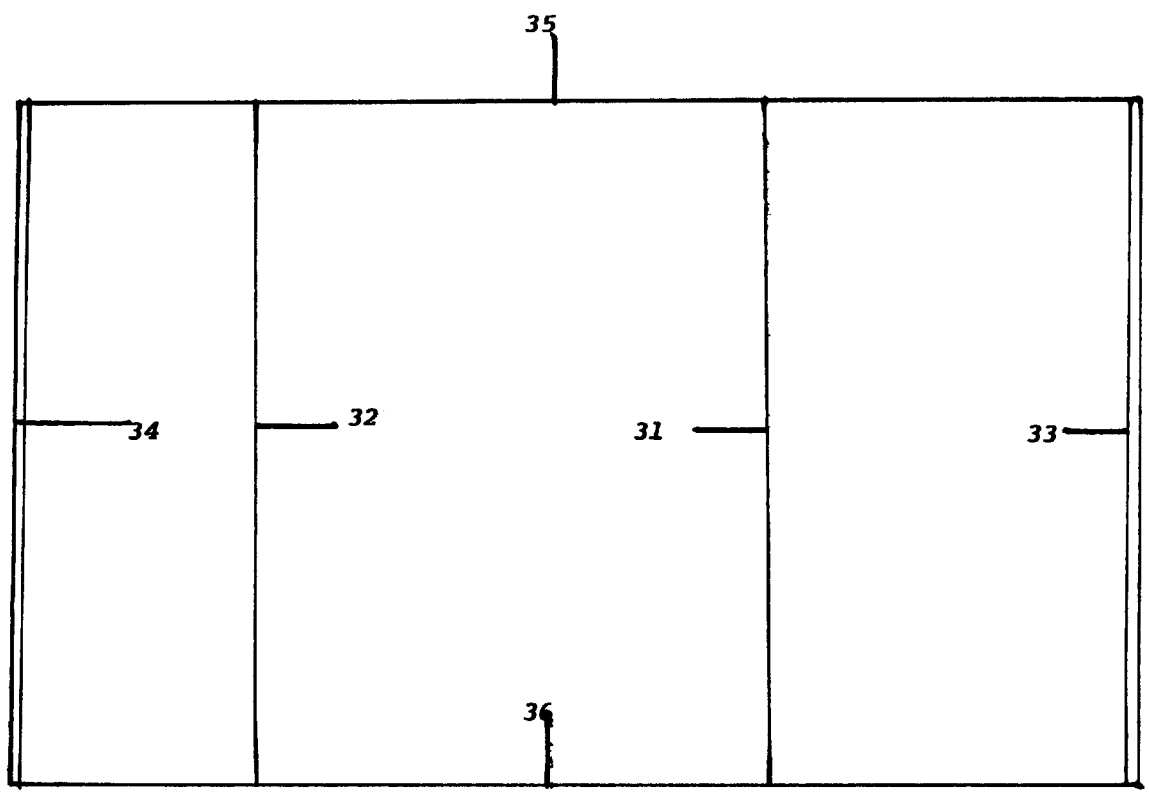
FIG. 4 is a view of an unassembled pillow case.
Figure 5:
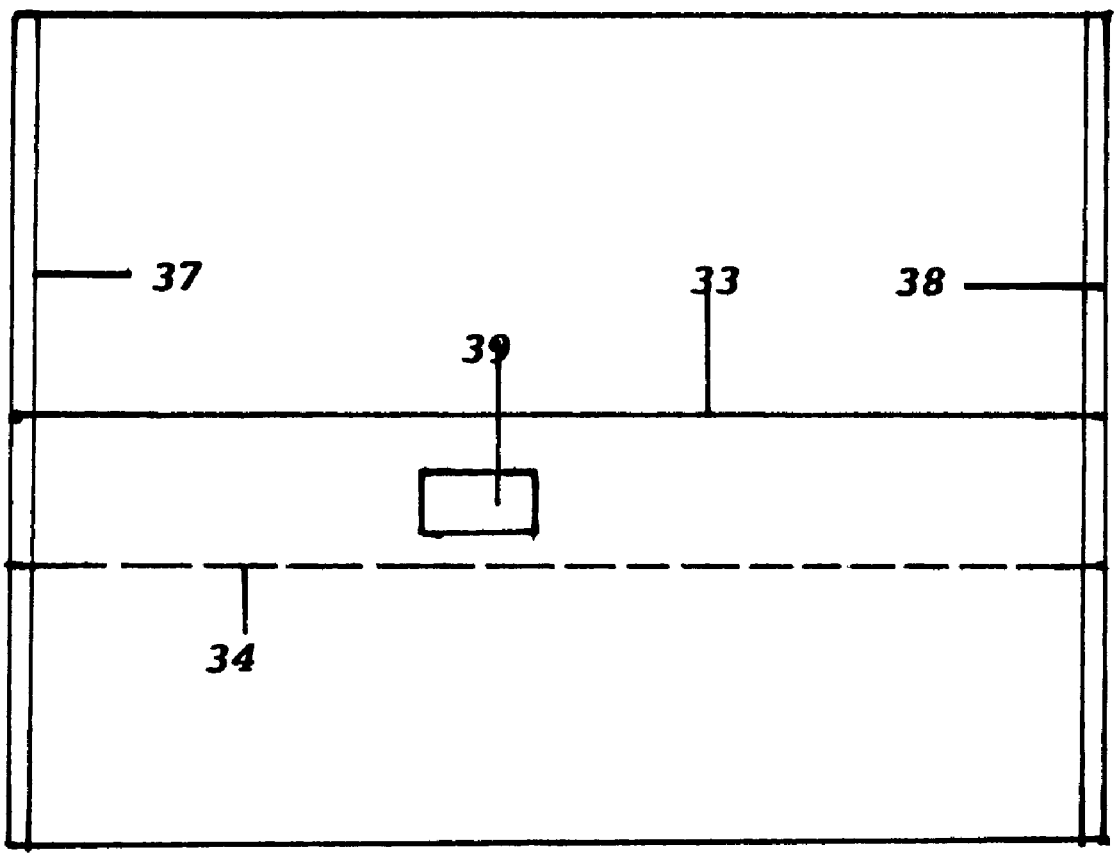
FIG. 5 is a view of a folded pillow case.

Once the pillow 16 is thusly mounted to the assembly of the present invention, the entire combination may be inserted into an enlarged pillow case 18 shown in FIG. 4 AND FIG. 5. Assuming that pillow case 18 fits somewhat snugly around the pillow 16, with the assembly of the present invention, the pillow case 18 will further assist in preventing movement between the pillow case 16 and the extended portion of the sheet member 14.

Using a piece of cotton or cotton blend fabric 48" in length and 26" to 36" in width, to accommodate a standard, queen and king size ordinary pillow, the enlarged pillow case is constructed. FIG. 4 is the flat unassembled view of pillow case 18. FIG. 5 has been folded and is ready for stitching.

Side 33 is folded and stitched with a ¼ inch hem to form a finished edge and is then folded at line 31, which is 8" from the finished edge of the fabric. Side 34 is folded and stitched with a ¼" hem to form a finished edge and is then folded at line 32, which is 16½" from the other finished edge of the fabric and will provide a finished overlap of 3½". FIG. 5 shows the enlarged pillow case folded to a dimension of 22" long by 26" to 36" wide. Seam 37 and Seam 38 are then sewn. A closure 39 of Velcro, a hook and loop fastener ¾" by 2" is then inserted on the underside of side 33 and 34, where they overlap and a pouch for the assembly is formed that will house a conventional pillow in the longer side and the pillow insert assembly in the smaller side of the enlarged pillow case 18 and enclosed by closure 39.

The overall combination of the present invention, as thusly assembled, will thereby include a conventional pillow 16 within an enlarged pillow case 18, but will further include the assembly made from wedge member 12 and sheet member 14. As can best be seen in FIG. 1, if the user places his or her head on the assembly with the user's head toward the right as shown in FIG. 1, the present invention will thus provide the user with a rounded surface upon which the back of the head and the neck of the user can be rested.

I claim:

1. An assembly adapted to receive a pillow and to enclose the pillow in a pillowcase in order to control the snoring and improve the sleep of the user of the assembly, said assembly comprising:

a) a wedge member made of resilient material having a generally quarter-cylinder shape, thereby defining a circumference including a first flat surface, a second flat surface and a curved surface;

b) a sheet member made of flat resilient material, said sheet member being attached to said wedge member and extending beyond said wedge member to form an elongated section, said elongated section having an upper surface which provides substantial friction when the pillow is mounted thereon, said elongated section of said sheet member and said wedge member together defining a space for receiving and holding the pillow; and c) a pillow case adapted to envelope said wedge, said sheet member and said pillow.

2. The assembly according to claim 1 in which said wedge member is made of resilient foam rubber.

3. The assembly of claim 1 in which said sheet member is made from a sheet of resilient foam rubber.

4. The assembly of claim 1 wherein said wedge member has a radius of approximately four inches and a width of approximately 12 to 20 inches.

5. The assembly of claim 1 wherein the sheet member has width of approximately 12 to 20 inches and a length substantially longer than said width.

6. The assembly of claim 1 wherein said sheet member is attached to said wedge member through the use of adhesive material.

7. The assembly of claim 1 wherein the sheet member is attached to said wedge member by wrapping said sheet member around said first flat surface, said curved surface and said and said second flat surface of said wedge member.

8. The assembly of claim 1 further comprising a pillow mounted to said elongated section of said sheet member and adjacent to said first flat surface of said wedge member.

9. The assembly of claim 1 wherein the pillow case is made of a cotton or cotton blend fabric.

10. The assembly of claim 1 wherein the pillow comprises a hook and loop fastening element.

11. The assembly of claim 1 wherein the pillow case has a finished dimension of 22" in length and approximately 26 to 36 inches in width.

* * * * *